(12) United States Patent
Lammers et al.

(10) Patent No.: US 10,639,192 B2
(45) Date of Patent: May 5, 2020

(54) DEVICE AND METHOD FOR ADMINISTERING A LIQUID DROP BY DROP

(71) Applicant: Sparkle Innovations B.V., Apeldoorn (NL)

(72) Inventors: Leonardus Hubertus Maria Lammers, Hoofddorp (NL); Hubertus Eduard Hilbrink, Apeldoorn (NL); Willem Frans Lichtenauer, Appeltern (NL); Johannes van der Heiden, Goirle (NL)

(73) Assignee: Sparkle Innovations B.V., Apeldoorn (NL)

( * ) Notice: Subject to any disclaimer, the term of this patent is extended or adjusted under 35 U.S.C. 154(b) by 435 days.

(21) Appl. No.: 15/301,275

(22) PCT Filed: Apr. 2, 2015

(86) PCT No.: PCT/NL2015/050213
§ 371 (c)(1),
(2) Date: Sep. 30, 2016

(87) PCT Pub. No.: WO2015/152721
PCT Pub. Date: Oct. 8, 2015

(65) Prior Publication Data
US 2017/0020727 A1    Jan. 26, 2017

(30) Foreign Application Priority Data
Apr. 4, 2014   (NL) ........................... 2012570

(51) Int. Cl.
*A61F 9/00* (2006.01)
*B65D 73/00* (2006.01)
(Continued)

(52) U.S. Cl.
CPC ........ *A61F 9/0008* (2013.01); *B29C 45/0003* (2013.01); *B29C 64/00* (2017.08);
(Continued)

(58) Field of Classification Search
CPC ...... A61F 9/0008; A61F 9/0026; A61F 15/00; A61F 2/1691; A61M 5/00; B65D 77/00; B65D 77/04
See application file for complete search history.

(56) References Cited

U.S. PATENT DOCUMENTS 5,607,410 A * 3/1997 Branch .................. A61H 35/02
                                                          604/295
5,954,233 A    9/1999 Kawashima et al.
(Continued)

FOREIGN PATENT DOCUMENTS

GB       2206794      1/1989
WO    2007/062361     5/2007
(Continued)

OTHER PUBLICATIONS

Patton (1977) "Pharmacokinetic evidence for improved ophthalmic drug delivery by reduction of instilled volume" Journal of Pharmaceutical Sciences, 66(7):1058-1059.

*Primary Examiner* — Tatyana Zalukaeva
*Assistant Examiner* — Gabriella E Burnette
(74) *Attorney, Agent, or Firm* — Edward J. Baba; Bozicevic, Field & Francis LLP

(57) ABSTRACT

The invention relates to a device for administering a liquid drop by drop, in particular an ophthalmic liquid. This administering device comprises a packaging filled with the liquid and an outflow channel for connecting to the packaging and comprising a perforation member at one end, which perforation member is received in a frame for mounting on the packaging. The invention further relates to an
(Continued)

Figure 3:
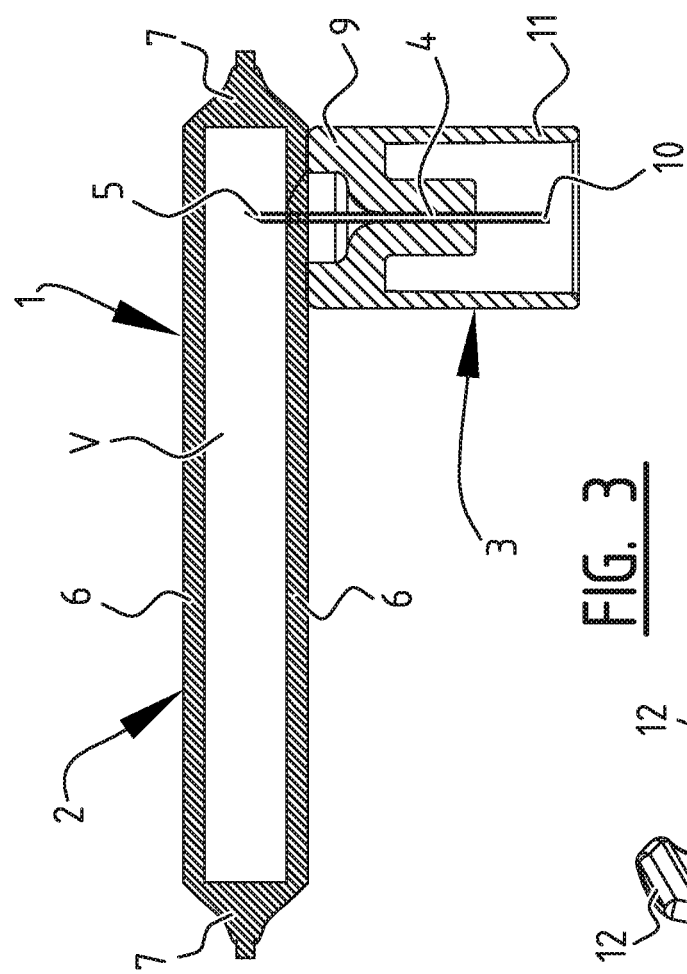

assembly of such an administering device and an outer packaging which comprises one or more receiving spaces for the administering device. The invention also relates to a method for manufacturing a frame for such an administering device. The invention also relates to a method for forming an administering device. The invention finally relates to a method for administering a liquid drop by drop.

30 Claims, 14 Drawing Sheets

(51) Int. Cl.
| | |
|---|---|
| *B65D 75/58* | (2006.01) |
| *B65D 77/04* | (2006.01) |
| *B29C 64/00* | (2017.01) |
| *B33Y 10/00* | (2015.01) |
| *B33Y 80/00* | (2015.01) |
| *B29C 45/00* | (2006.01) |
| *B29D 12/00* | (2006.01) |
| *B29K 23/00* | (2006.01) |
| *B29K 71/00* | (2006.01) |
| *B29L 31/00* | (2006.01) |

(52) U.S. Cl.
CPC .............. *B29D 12/00* (2013.01); *B33Y 10/00* (2014.12); *B33Y 80/00* (2014.12); *B65D 73/0035* (2013.01); *B65D 75/5872* (2013.01); *B65D 77/0473* (2013.01); *B29K 2023/12* (2013.01); *B29K 2071/00* (2013.01); *B29L 2031/753* (2013.01)

(56) References Cited

U.S. PATENT DOCUMENTS

| | | | | |
|---|---|---|---|---|
| 2007/0191780 | A1* | 8/2007 | Modi | A61M 5/288 604/187 |
| 2011/0208138 | A1* | 8/2011 | Hilbrink | A61F 9/0008 604/290 |

FOREIGN PATENT DOCUMENTS

| | | | | |
|---|---|---|---|---|
| WO | 2008/062203 | | 5/2008 | |
| WO | WO-2008062203 | A2 * | 5/2008 | .............. A61J 1/067 |
| WO | 2010/041941 | | 4/2010 | |
| WO | 2010/084393 | | 7/2010 | |
| WO | WO-2010084393 | A1 * | 7/2010 | .............. A61J 1/067 |
| WO | WO-2015061401 | A1 * | 4/2015 | ........... A61F 2/1691 |

* cited by examiner

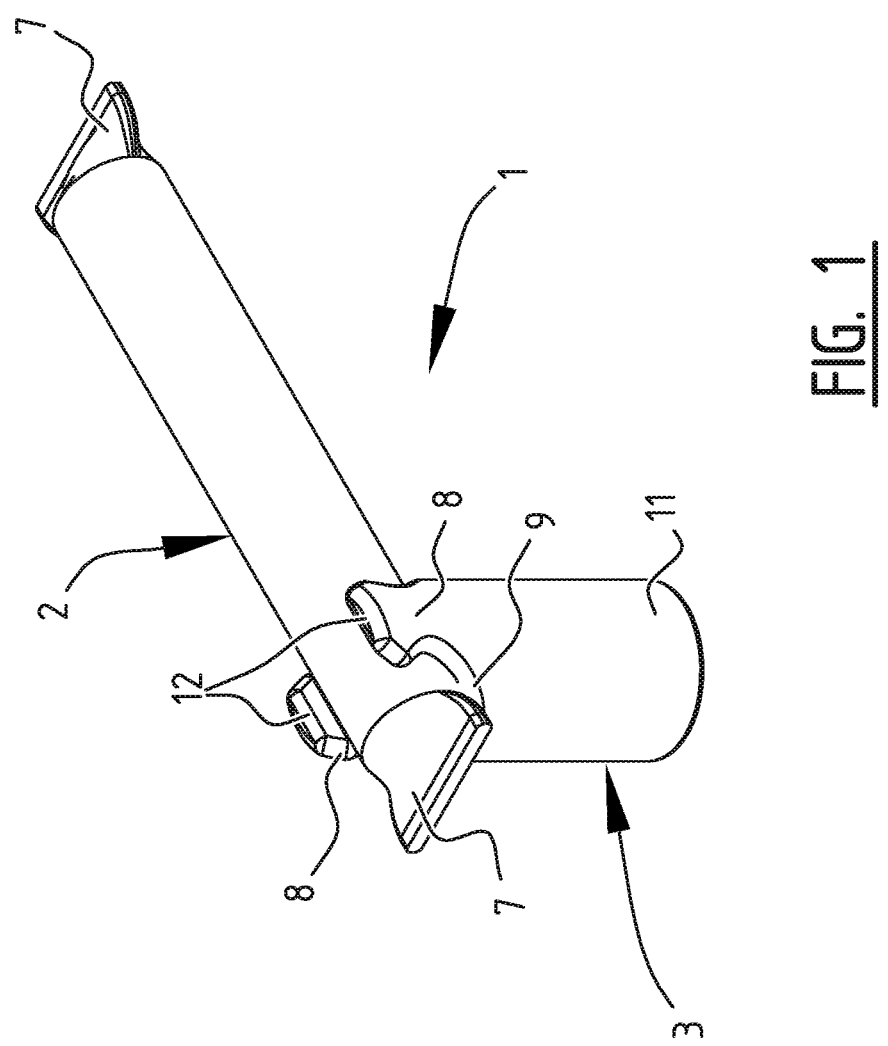

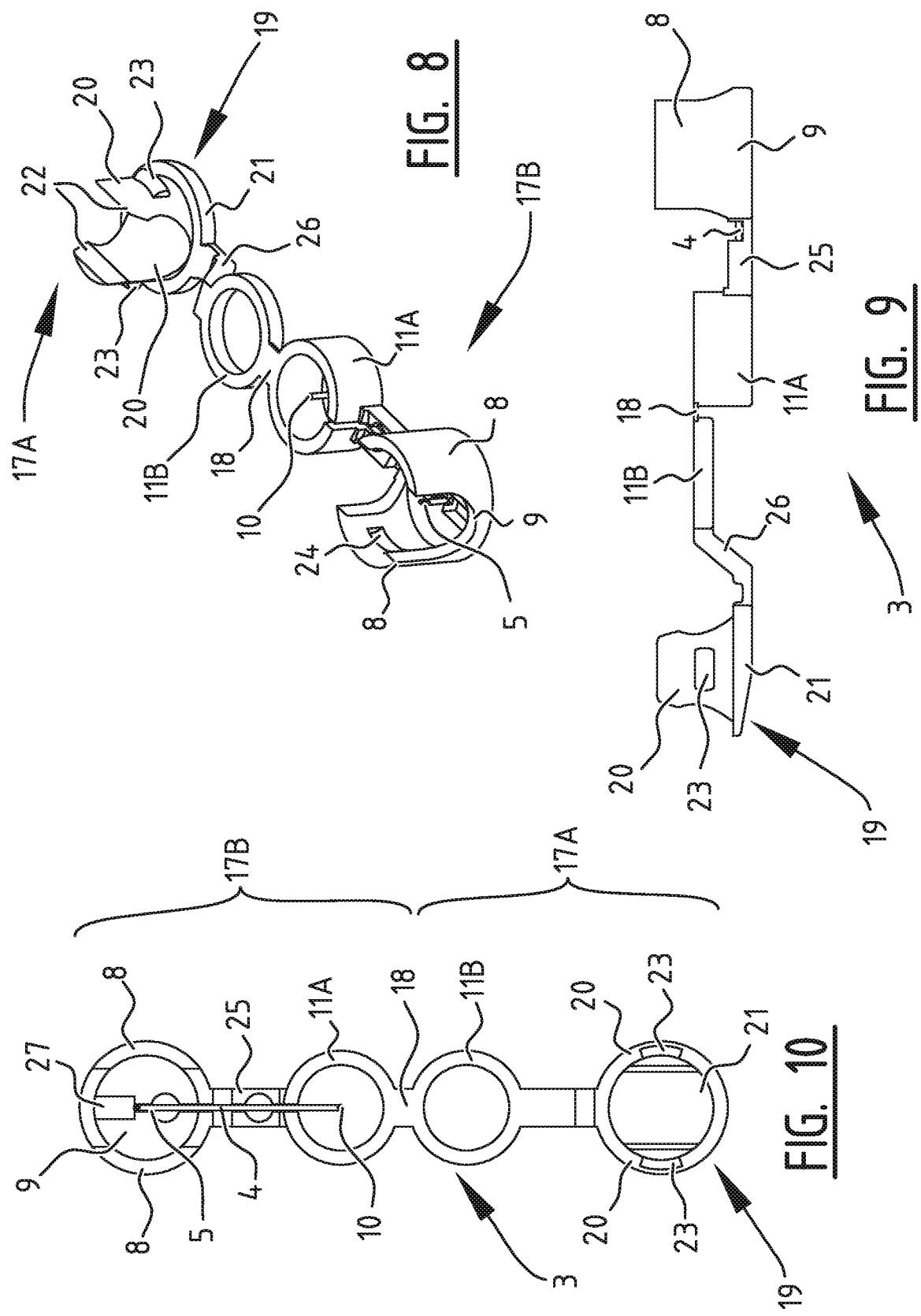

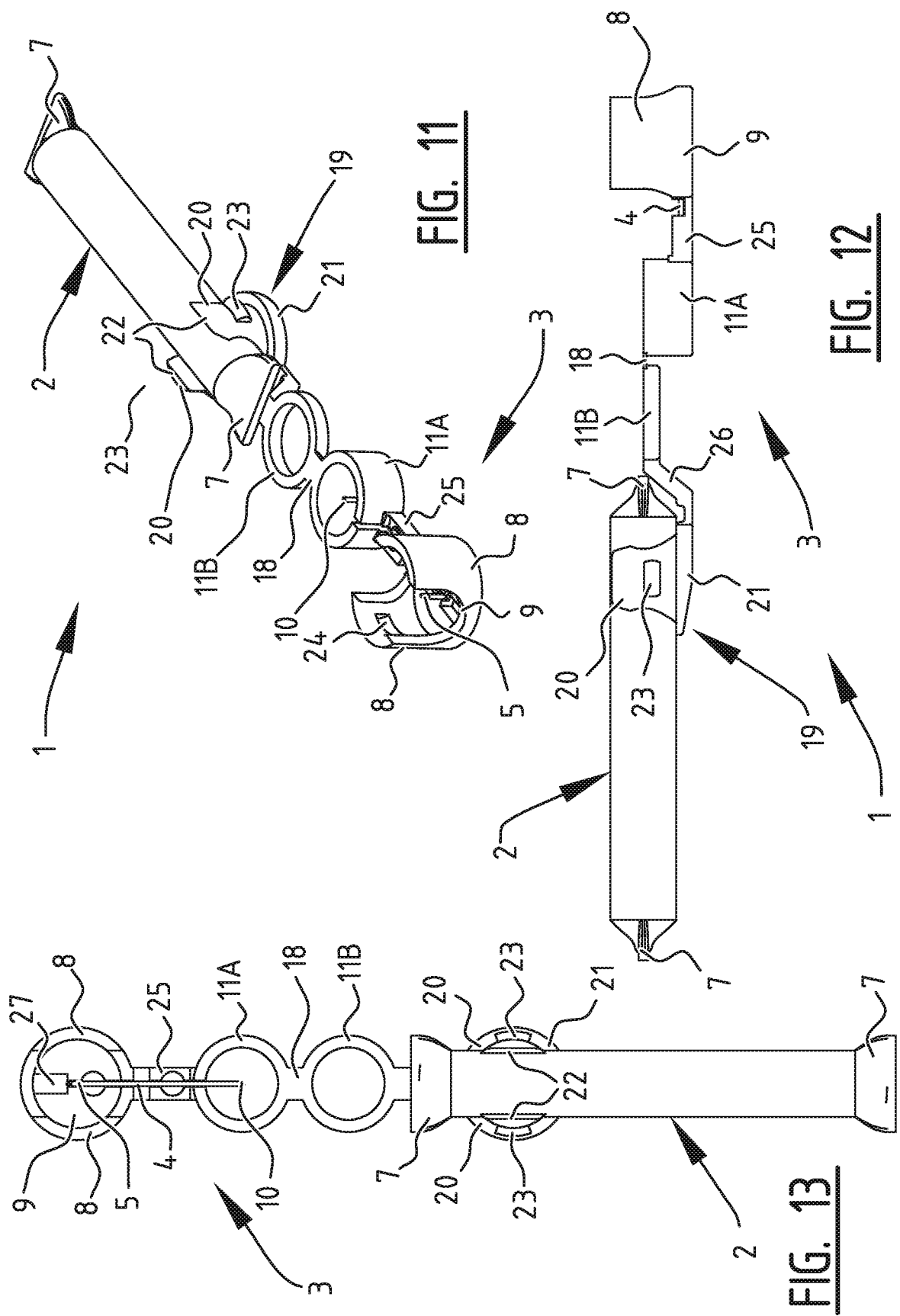

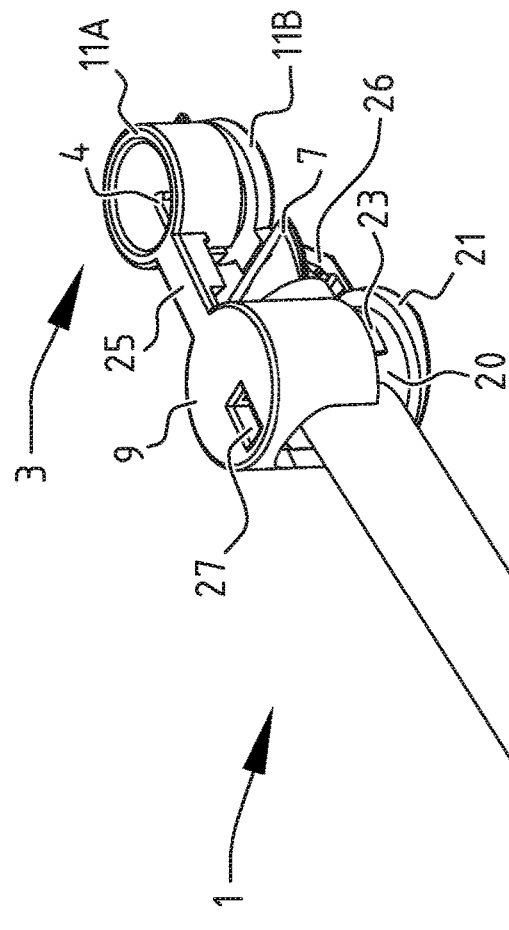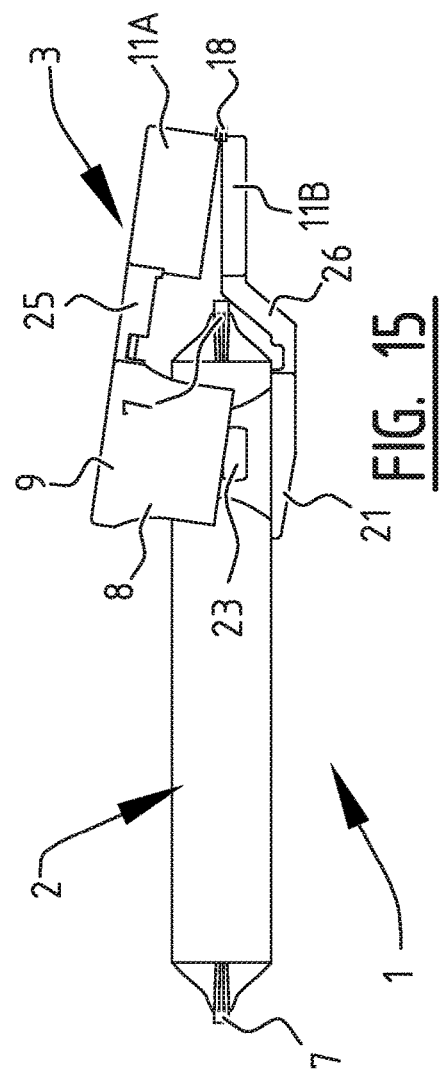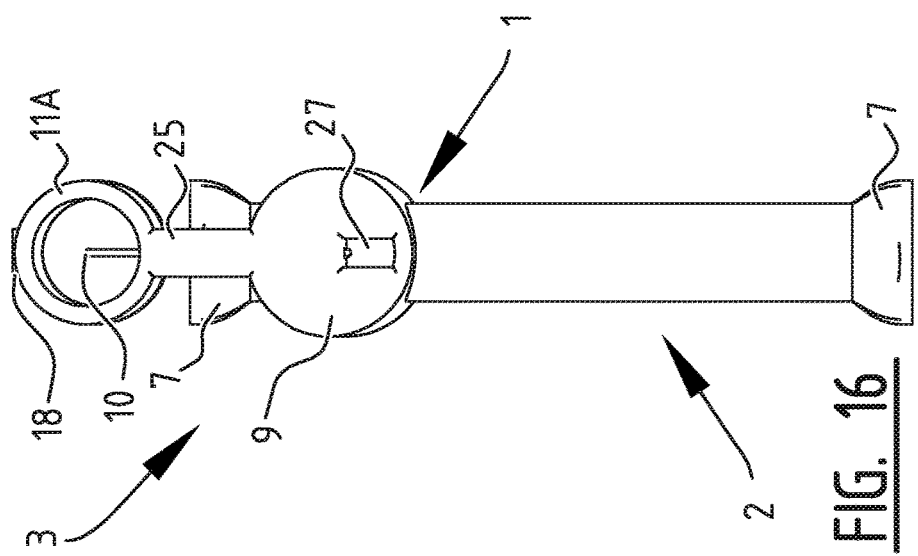

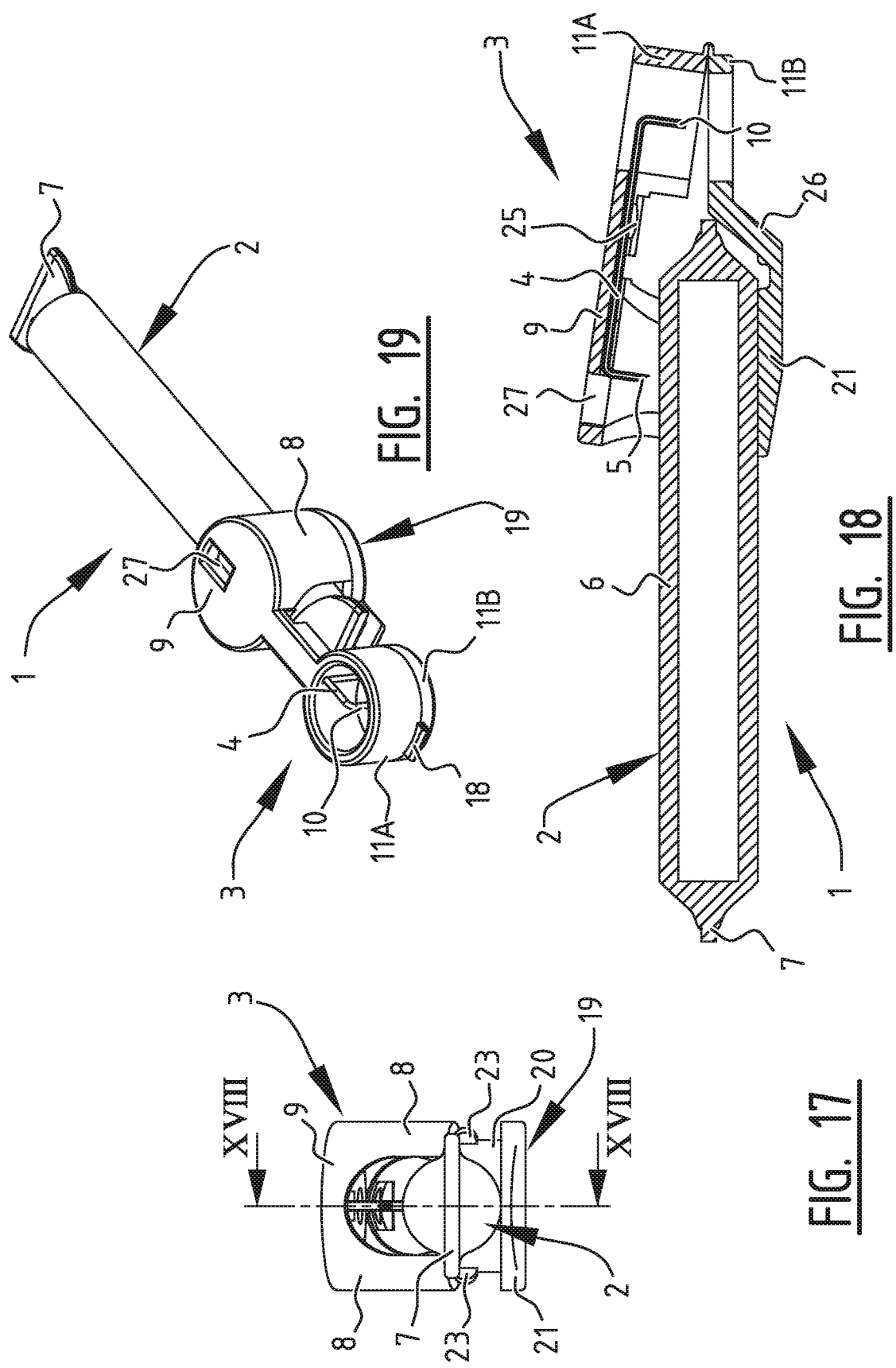

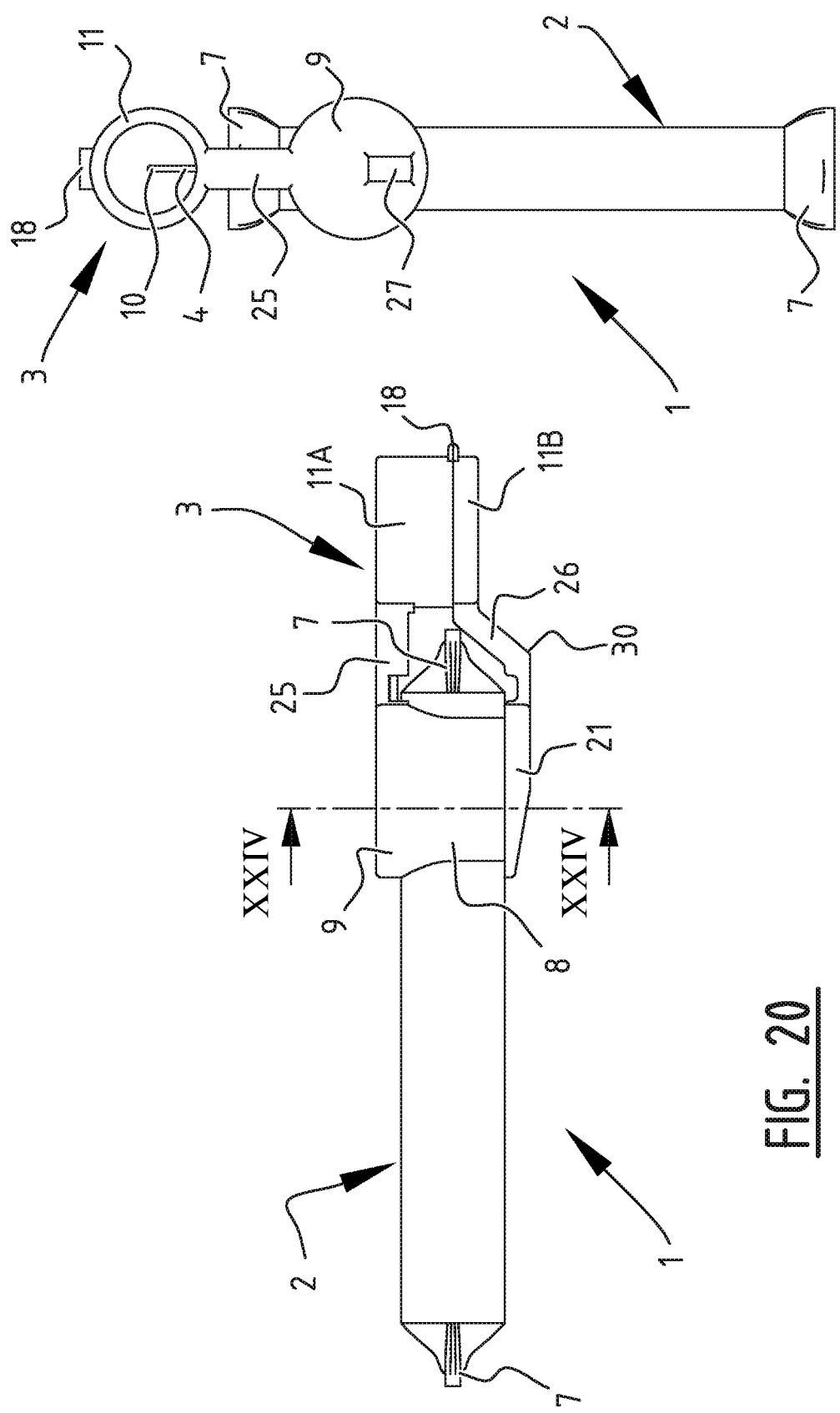

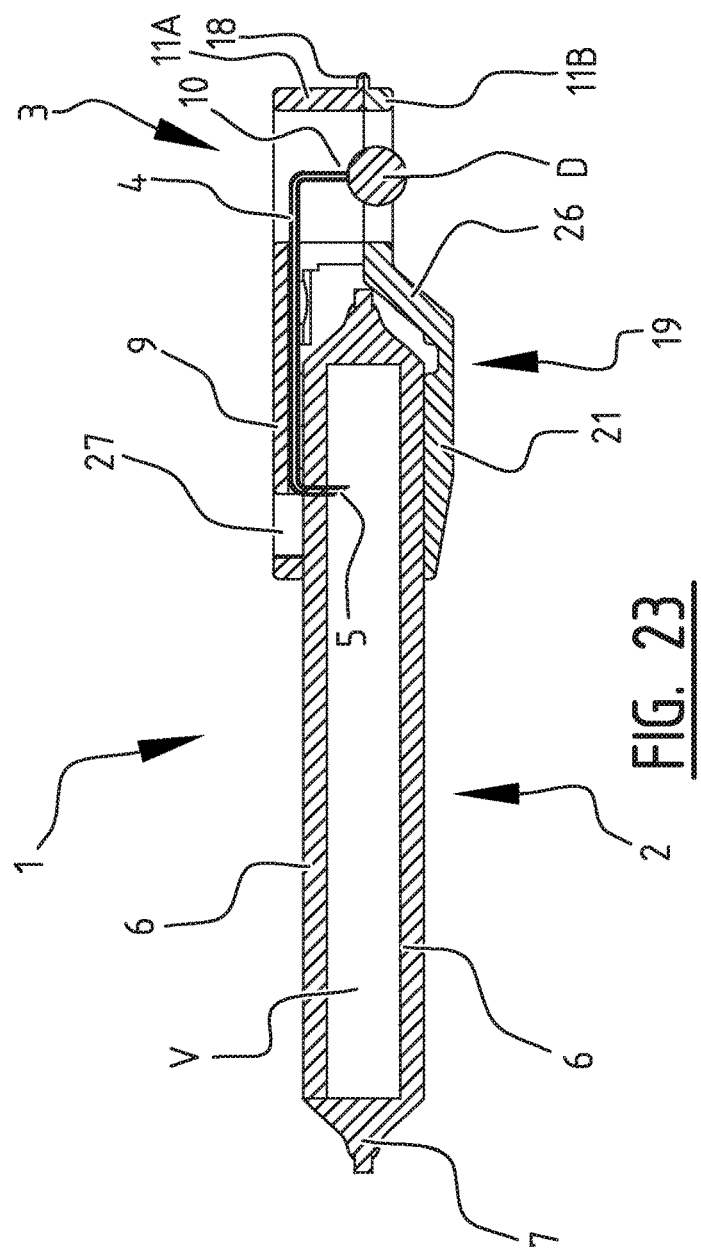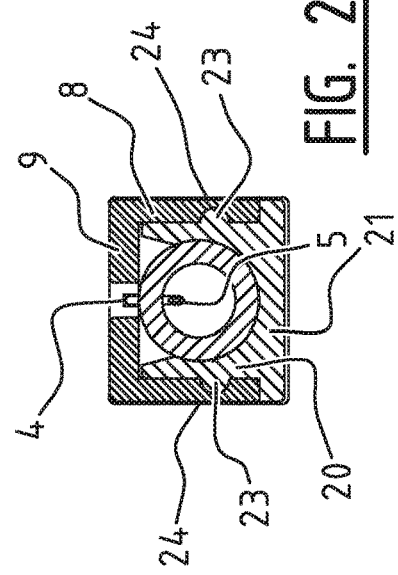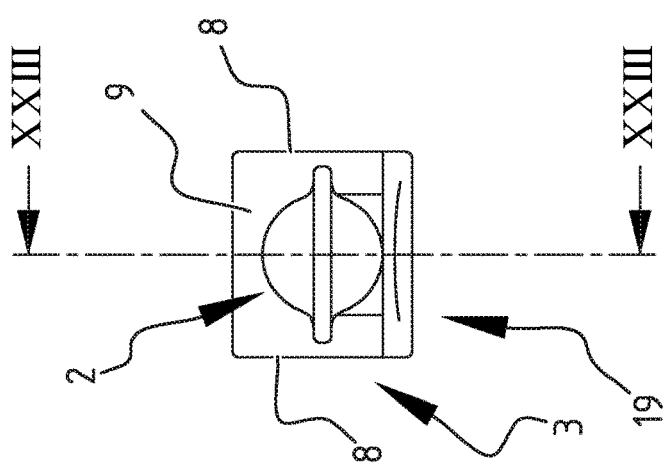

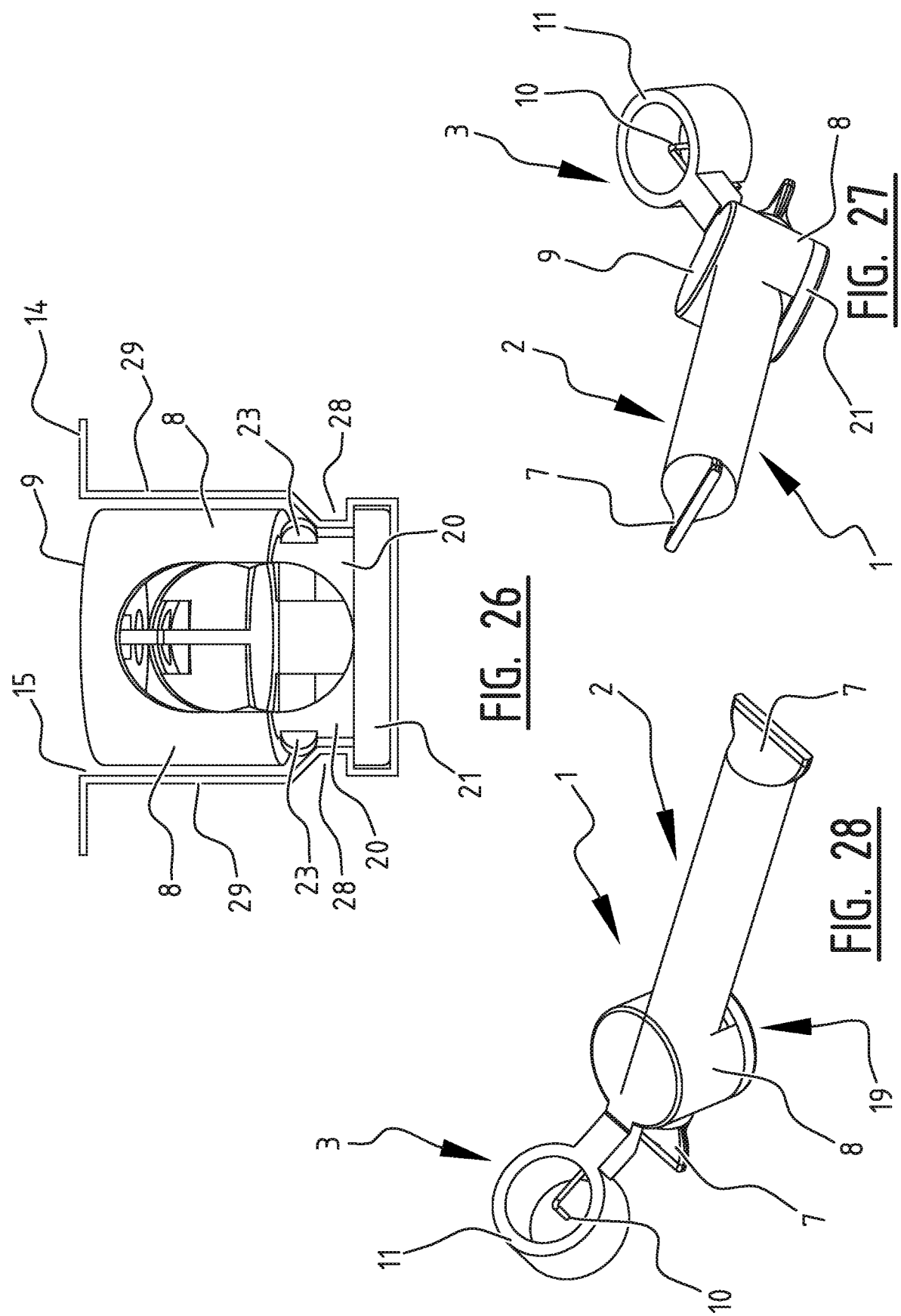

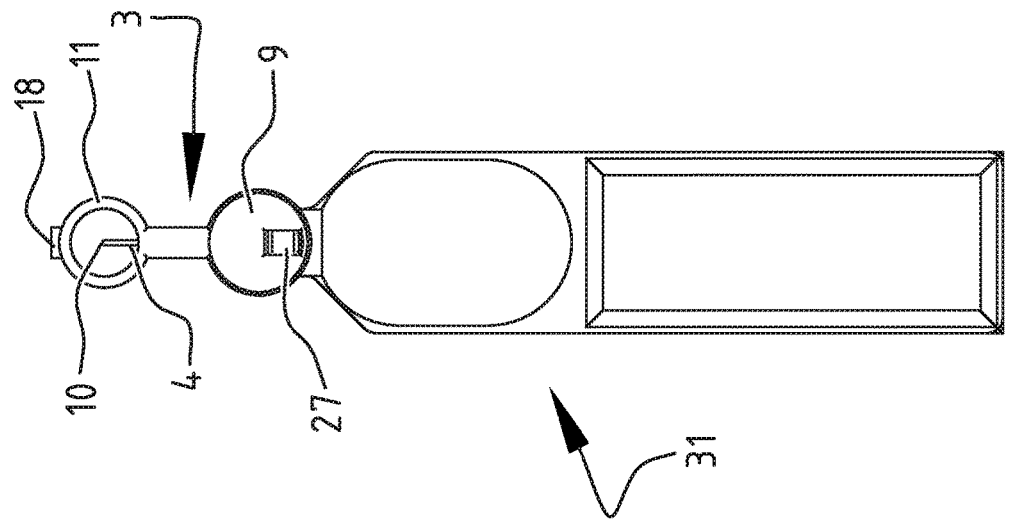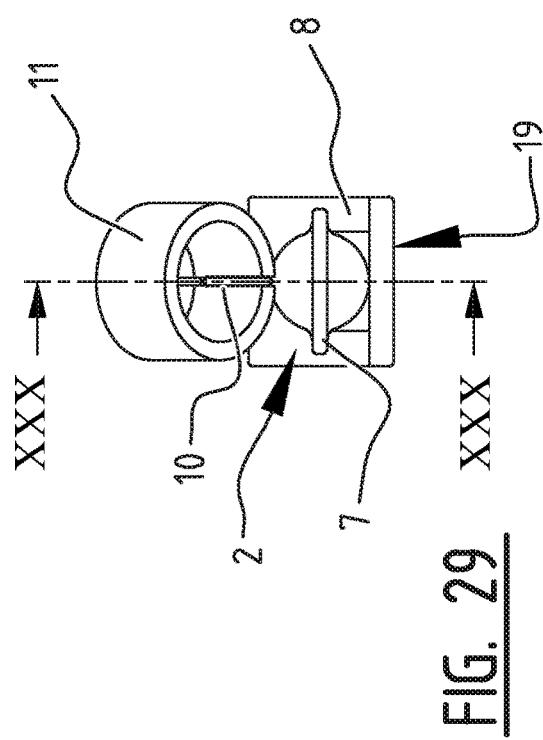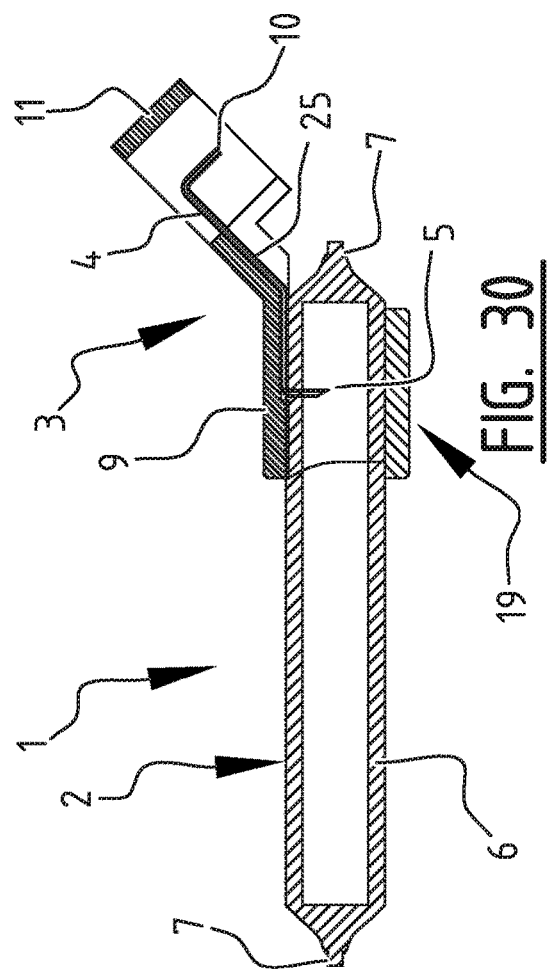

DEVICE AND METHOD FOR ADMINISTERING A LIQUID DROP BY DROP

The invention relates to a device for administering a liquid drop by drop, in particular an ophthalmic liquid, comprising a packaging at least partially filled with the liquid and an outflow channel for connecting to the packaging and comprising a perforation member at one end. Such an administering device with which eye-drops can be administered in controlled manner with a reproducible volume and a guaranteed quality is known from the earlier patent application of applicant with publication number WO 2010/041941 A1.

Devices known heretofore for administering eye-drops can be divided into two groups; droppers for multiple use and droppers for once-only use. "Multiple use" is understood to mean the use at different moments or points in time with long intervals. Conversely, "once-only use" is understood to mean the use at a determined moment or point in time. A plurality of eye-drops can be delivered here, optionally into both eyes of the user.

Administering devices for multiple use are provided with a relatively large container, often a plastic or glass bottle, in which is received a quantity of liquid sufficient for administering for some time at regular intervals. A dropper is mounted on the neck of this container. These administering devices have a number of drawbacks.

In view of their prolonged use the liquids in these devices thus often comprise preservatives which can be harmful to the eye. In addition, it is often not known when the device was taken into use, so that there is the risk of it being used for too long. In this case micro-organisms could grow in the liquid, despite the preservatives, which could result in eye infection and even blindness. The growth of micro-organisms is further enhanced by the liquid coming into contact with ambient air drawn in each time it is administered. Such large administering devices are moreover sometimes used for different patients, which can result in cross-infection between these patients.

The known administering devices for multiple use dispense droplets whose size can vary quite considerably. These drops are in any case relatively large in proportion to the volume of tear-water in the eye. It is known from the literature (T. F. Patton, "Pharmacokinetic evidence for improved ophthalmic drug delivery by reduction of instilled volume", Journal of Pharmaceutical Sciences, 66(7), pp. 1058-1059, July 1977) that relatively small eye-drops can have a comparable therapeutic effect. Large drops have the drawback, among others, that a part of the excess liquid can be taken up directly into the blood through the tear-duct, whereby side-effects can be caused.

Administering devices for once-only use usually consist of a relatively small plastic container with an integrated dropper. Such devices for once-only use also have a number of drawbacks.

As a result of their small dimensions these devices thus provide hardly any space for the purpose of arranging thereon information relating for instance to use. The information must therefore be in relatively small print, whereby it will be hardly legible to the users, who will often have poor eyesight. Owing to their small dimensions these administering devices are also difficult to handle for patients who will often be somewhat older. While different aids have been proposed for improving handling of the small devices, these are not always found to be effective.

These small devices are further often intended to be opened by a cap being broken or torn off, the so-called "twist-off". The dimensions of the thus created administering opening are not always the same, and often too large, thereby resulting in large drops. The tear-off edge is also often of irregular form, whereby the drop size can vary considerably. In addition, if it comes into contact with the eye, the tear-off edge can result in damage to the eye.

Finally, the cap can often be re-placed in such administering devices for once-only use, whereby there is the risk of the device being used more than once. There is then once again the risk of infection of the liquid.

Known from the above mentioned document WO 2010/041941 A1 is a device for administering eye-drops, wherein a packaging filled with the eye-drop liquid is placed in a receiving space in a box-like frame. The receiving space is slightly wider here than the packaging. The box-like frame is provided with a cover having inclining displacing members thereon. When the cover is closed these displacing members press the packaging to one side of the receiving space. Further incorporated in the frame is an outflow channel with a sharp outer end which protrudes into the receiving space and an outflow opening which protrudes through a surface of the box. When the packaging is pressed to the one side of the receiving space, it is pressed with its side wall against the sharp point of the outflow channel whereby a liquid connection is formed between the packaging and the outflow channel. Pressure is exerted on the packaging by now pressing on a deformable part of the cover, whereby the liquid is dispensed drop by drop via the outflow channel.

This known administering device has the drawback of being relatively voluminous and complex, and therefore in fact too expensive for once-only use. There is therefore the risk that users will use the device more than once, also because it can be easily stored in easily manageable form. There is the further risk that users will try to open the cover so as to thus replace the packaging and then reuse the device. This all carries the risk of infection. The user must further place the packaging with his/her hand in the frame of the administering device, which also carries a risk of infection. In addition, administering with this device cannot be properly monitored, particularly not by third parties. This is a drawback when the liquid must be used under the supervision of a therapist. It is also difficult for the user him/herself to position the known administering device in the correct manner above his/her eye.

The invention now has for its object to provide an administering device of the above described type wherein these drawbacks do not occur, or at least do so to lesser extent. This is achieved according to the invention with a dispensing device of the above described type wherein the perforation member is received in a frame for mounting on the packaging. By making use of the frame which is mounted on the packaging instead of a frame in which the packaging is received in its entirety, a simpler and less expensive construction is obtained which is more readily suitable for once-only use.

The packaging is preferably at least partially tubular and the frame can be mounted round the tubular part of the packaging. The frame can thus be used with different types of packaging, small hose-like packagings as well as packagings in the form of a plastic bottle with or without a neck. "Tubular" is understood here to mean not only a cylindrical cross-sectional form but also an elliptical or even a prismatic section with rounded angles.

This can be realized in simple manner when the frame comprises a substantially U-shaped part with two arms which extend on either side of the tubular part of the packaging and a bridge piece connecting the arms and carrying the perforation member. Placing this frame with the arms on either side of the packaging automatically achieves that the perforation member protrudes into the part of the packaging located between the arms. The bridge piece functions here as a stop, thereby preventing the perforation member passing straight through the packaging to the outside again.

For a good mounting of the frame on the packaging it is recommended that at least the tubular part of the packaging is resiliently deformable and is clamped between the arms.

When the arms co-act with an enclosing part arranged on a side of the tubular part of the packaging opposite the bridge piece, the packaging can be wholly enclosed in the frame. A particularly reliable attachment is thus obtained which is not easy to detach.

The arms are preferably movable relative to the enclosing part between a transport position, in which the outflow channel is not yet connected to the packaging, and a position of use in which the perforation member of the outflow channel protrudes into the packaging. The packaging and the frame can thus be assembled under controlled conditions at a production location and transported in assembled state to an end user who then need only bring the administering device into the position of use with a simple operation.

When the arms are locked relative to the enclosing part in the position of use, the administering device can no longer be taken apart, so preventing the possibility of the frame being used more than once and with different packagings.

For the purpose of forming the sought uniform drops the outflow channel is provided at an end opposite the perforation member with an outflow nozzle. In order to protect the outflow nozzle from contamination and damage, but also to protect the user from injury, the outflow nozzle is preferably received with clearance and recessed into a protective member which forms part of the frame. The protective member preferably takes the form of a ring, this shape corresponding well to the shape of the drops dispensed by the administering device. In order to assist the user in orienting the outflow nozzle such that the drops falling therefrom enter his/her eye, it is recommended that a centre line of the ring is parallel to or coincides with the outflow nozzle. The ring can then be used as reference.

In a structurally simple embodiment the outflow channel is substantially straight and the protective number lies substantially in line with a part of the frame mounted on the packaging.

Preferably however the outflow channel has at least one bend and the protective member is open. The outflow nozzle is hereby always readily visible both to the user and optionally to a therapist when the user does not administer the drops him/herself.

For reasons of production engineering it is recommended that the frame has an opening through which the perforation member is accessible. This latter can thus still be shaped after mounting in the frame.

A structurally simple and compact device is obtained when the protective member is connected to a part of the frame carrying the perforation member, and the outflow channel extends between this frame part and the protective member.

The protective member, the bridge piece and the arms are preferably formed as one body, and the outflow channel is attached to this body or integrated therein. The number of components of the administering device is thus minimized.

When the enclosing part is connected pivotally to the body, the frame can be easily folded round the packaging. It is also recommended in this case that the enclosing part is formed integrally with the body, whereby the number of individual components is limited still further.

In order to make the frame easy to handle despite the small dimensions and enable simple folding-together thereof, it is recommended that it is formed by a first half comprising the enclosing part and a part of the protective member, and a second half which is connected pivotally thereto and comprises a complementary part of the protective member and the bridge piece and the arms.

The outflow nozzle and/or the outflow channel are preferably configured to form drops with a volume of 1 to 50 µl, preferably 2 to 20 µl, and more preferably 3 to 10 µl. According to the scientific literature, such small drops are highly effective. The inventors are of the opinion that the complex composition of the ocular fluid should be respected as much as possible during treatment with eye-drops and must not be washed away unnecessarily.

It is recommended here that the outflow nozzle is defined by a tubular outer end of the outflow channel, the external diameter of which amounts to a maximum of 2 millimetres. The external diameter of the outflow nozzle more preferably amounts to a maximum of 1 millimetre, and most preferably even to only 0.5 millimetre or less. The inventors have had the insight that, liquid properties and ambient properties being equal, the drop size is not so much related to the throughflow area of the channel through which the eye-drops are dispensed, but rather to the outer diameter thereof.

The invention further relates to an assembly of an administering device as described above and an outer packaging which comprises a receiving space for the administering device. Making use of such an outer packaging with a receiving space enables the administering device to be supplied to a user in wholly or partially assembled state. The administering device can then be assembled and optionally sterilized under controlled conditions, thereby minimizing the risk of infection.

A structurally simple embodiment is obtained here when the receiving space comprises a recess for the packaging and a recess for at least a part of the frame which are formed in a surface. The outer packaging can then take the form of a so-called blister pack.

In order to prevent the possibility of the packaging being taken out of the outer packaging in not yet activated state, the receiving space is preferably configured to fix the device as long as it is in a transport position and not ready for use. This can be achieved in structurally simple manner when the fixation means comprise a deformable part of the wall of the receiving space. This deformable wall part is pressed outward by an activating operation and the device can be taken out of the outer packaging.

In order to enable easy removal of the administering device from the outer packaging, the frame and a part of the receiving space preferably define a tilting point. By pressing on one side of the device a part of the device located on the other side of the tilting point then moves upward out of the receiving space.

Since the (ophthalmic) liquids for which the administering device is particularly intended usually form part of a therapy lasting for some time, it is recommended that the outer packaging comprises a plurality of receiving spaces as well as space for arranging an information carrier or printed information. A user can thus collect a number of doses of the liquid at one time from a pharmacy. The larger outer packaging moreover provides sufficient space for printing for instance instructions for use thereon as well as information about the nature and origin of the product which is important for quality control. Because the administering device is only taken out of the receiving space when used, it remains coupled to the information carrier until the moment of use. This is an important requirement for pharmaceutical packages.

The invention further comprises a method for manufacturing a frame for an administering device of the above described type. According to the invention this method comprises the steps of:
forming a body comprising a bridge piece, arms and a protective member, and
connecting an outflow channel with a perforation member to the body.

A frame is thus formed with a minimum number of operations. An opening is preferably formed in the body, and a bending tool is inserted into the opening for the purpose of bending the channel. The channel can thus be installed in straight form in the body, and bent into the correct form only later. Problems with the alignment of the channel, the perforation member and the outflow nozzle are hereby prevented.

A simple and cost-effective production of the frame is achieved when the body is formed from plastic, particularly by injection moulding or 3-D printing.

The invention further relates to a method for forming an administering device of the above described type. According to the invention this method comprises the steps of:
a) providing a packaging at least partially filled with liquid,
b) providing a frame with an outflow channel and a perforation member, and
c) mounting the frame on the packaging such that the perforation member pierces the packaging and brings about a connection between the interior of the packaging and the outflow channel.

The administering device can be formed in simple manner by pressing or clamping the part of the frame carrying the perforation member onto the packaging.

When the frame comprises an enclosing part connected pivotally to the body, and is mounted on the packaging by folding the body and the enclosing part together around the packaging, the frame can on the one hand be produced in simple manner because all components lie in one plane and are readily accessible, and the connection to the packaging can then be realized in simple manner.

In order to enable forming of the administering device at a production location and subsequent transport to an end user it is recommended that step c) comprises the sub-steps of:
c1) connecting the frame to the packaging in a transport position in which the outflow channel has not yet been connected to the interior of the packaging, and
c2) displacing the frame from the transport position to a position of use in which the perforation member protrudes into the packaging.

Finally, the invention relates to a method for administering a liquid drop by drop, in particular an ophthalmic liquid. According to the invention this method comprises of taking an administering device as described above in the hand, mounting the frame on the packaging, wherein the perforation member pierces a wall of the packaging and brings about a connection between the interior of the packaging and the outflow channel, positioning the device above a recipient and exerting pressure on the packaging in order to urge the liquid dropwise therefrom. A recipient in the sense of the invention is here for instance an eye of the user.

The pressure can be exerted here on a deformable part of the wall of the packaging. Because the frame leaves the packaging largely clear, the user can exert pressure directly thereon, whereby an accurate dosage is achieved.

As stated, it is recommended that the frame is connected to the packaging in a transport position in which the outflow channel has not yet been connected to the interior of the packaging, and is mounted on the packaging by being displaced to a position of use in which the perforation member protrudes into the packaging. This guarantees that the liquid is sterile up to the moment of activation.

When the administering device is received in a receiving space in an outer packaging and the frame is mounted on the packaging while the packaging is situated in the receiving space, the packaging is properly supported during this operation, this increasing convenience of use, particularly in the case of relatively small packagings.

When the channel comprises an outflow nozzle surrounded by an open protective member and administering is monitored by being observed from a side of the protective member lying opposite the outflow nozzle, a therapist can administer the drops in well-controlled manner.

Figure 4:
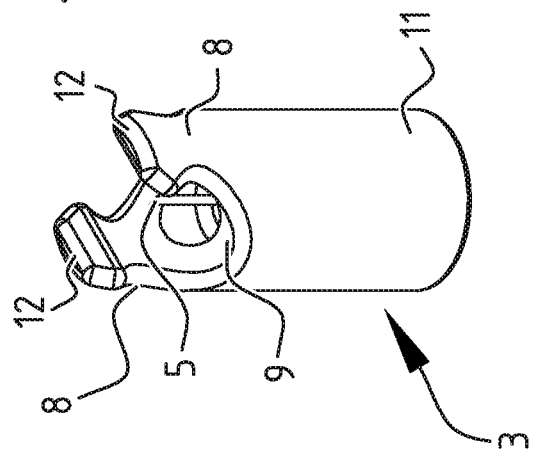
Figure 2:
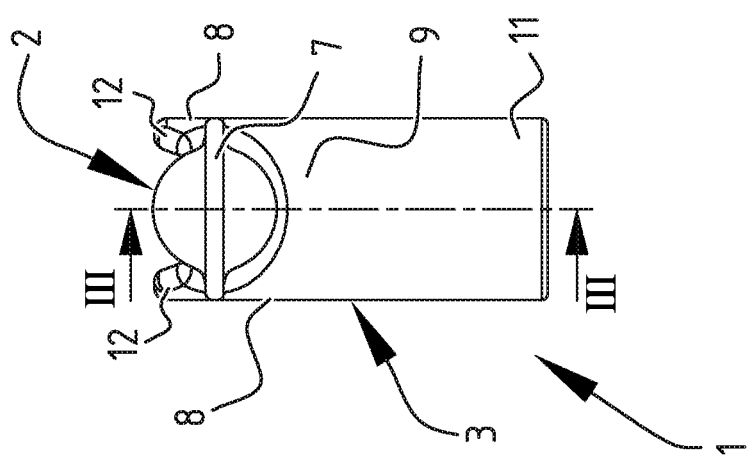
Figure 5:
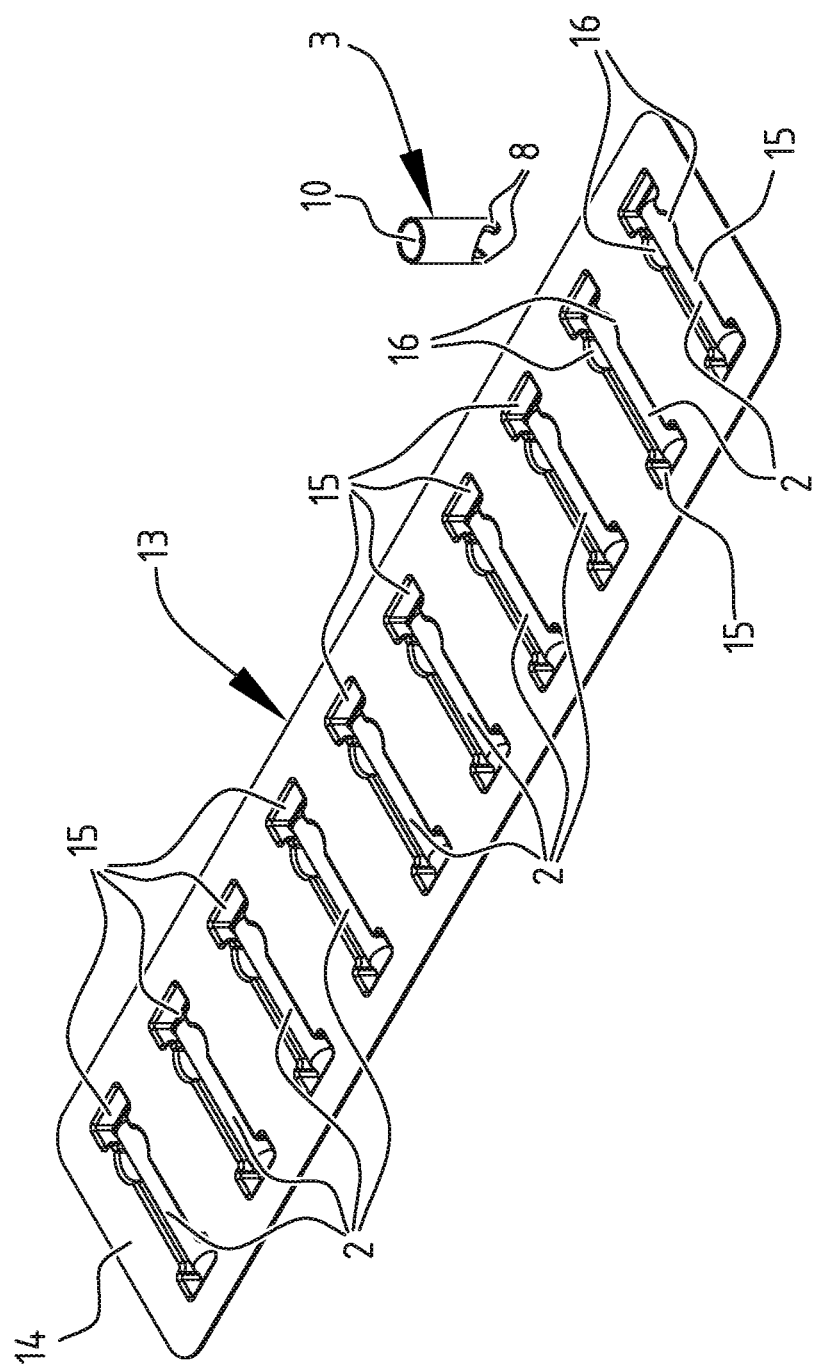
Figure 6:
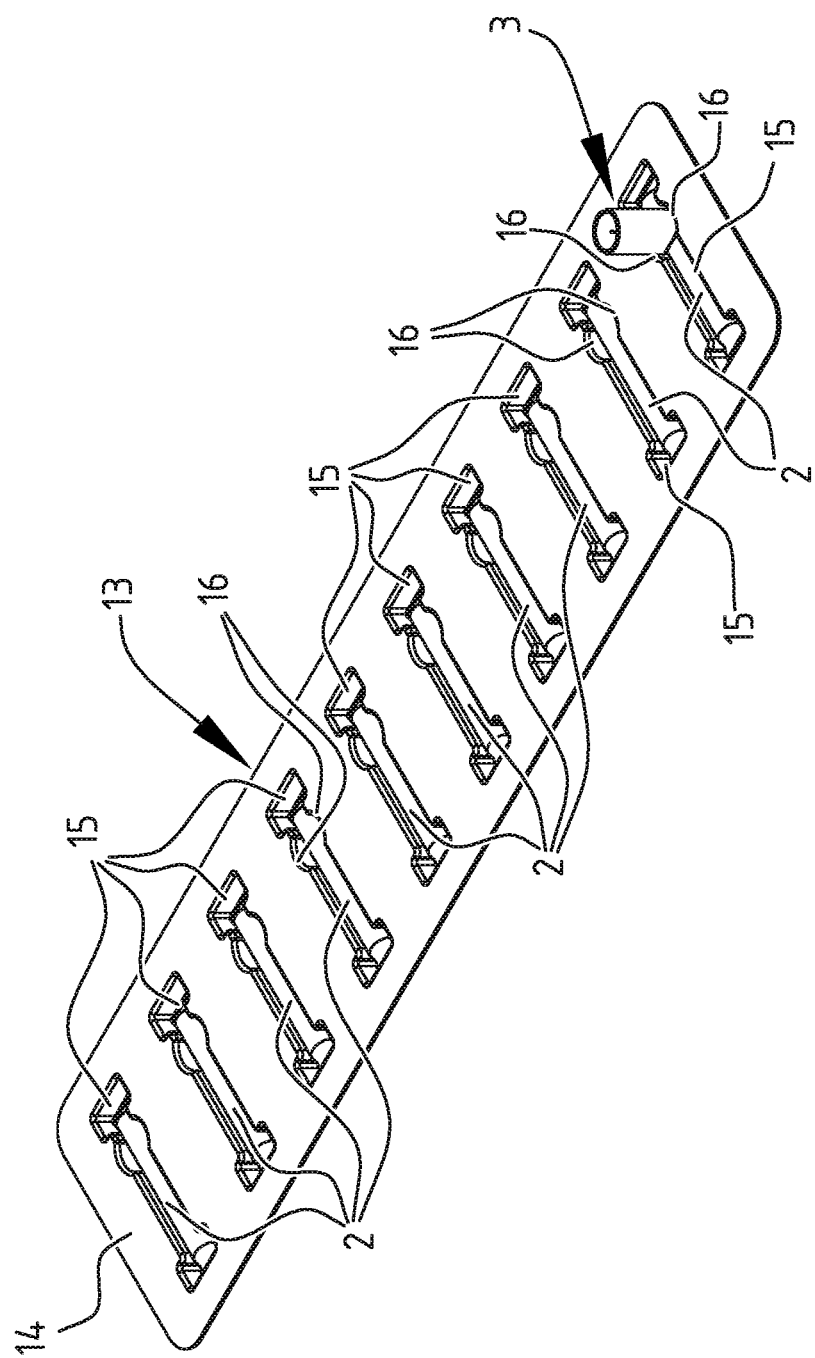
Figure 7:
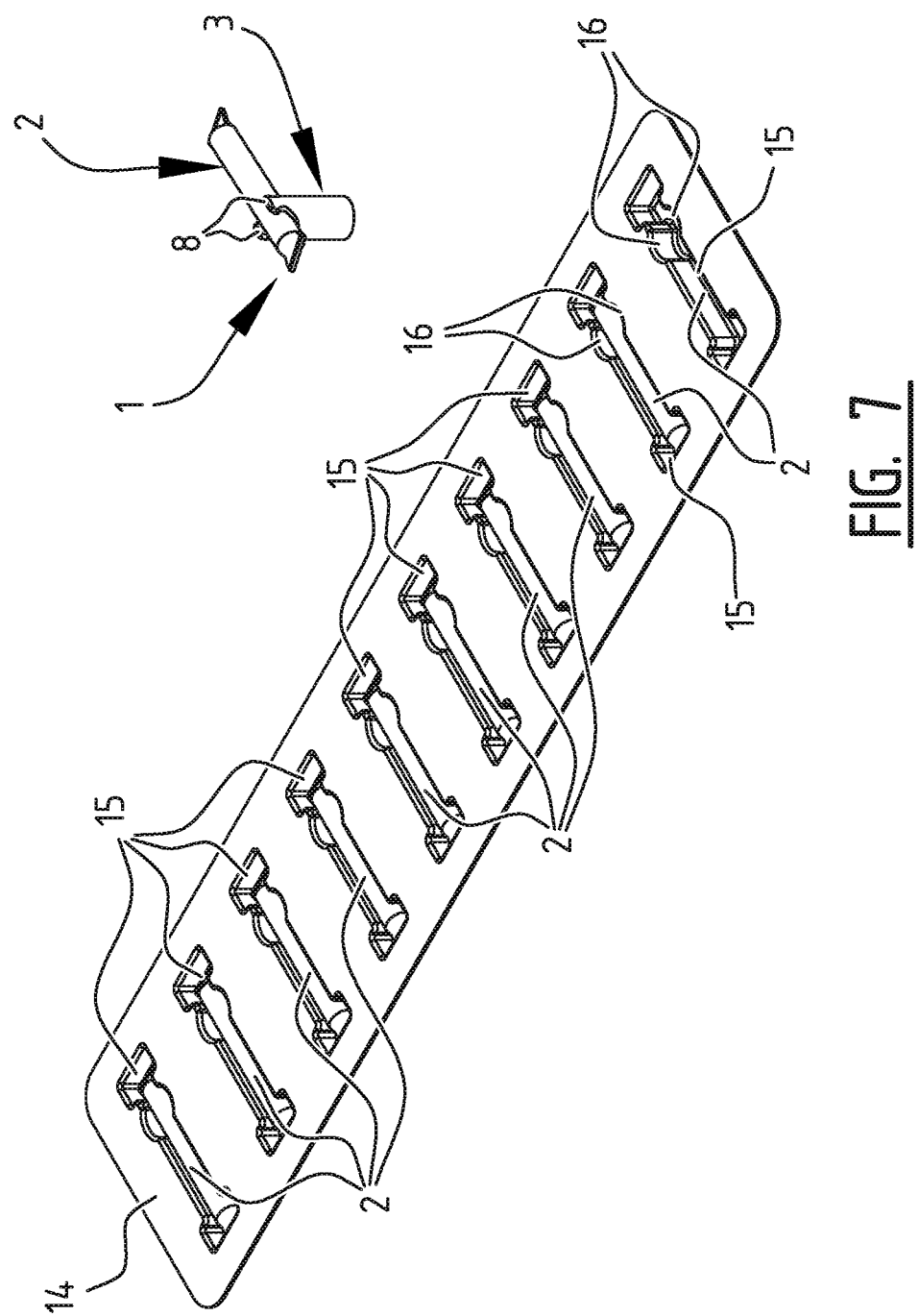
Figure 25:
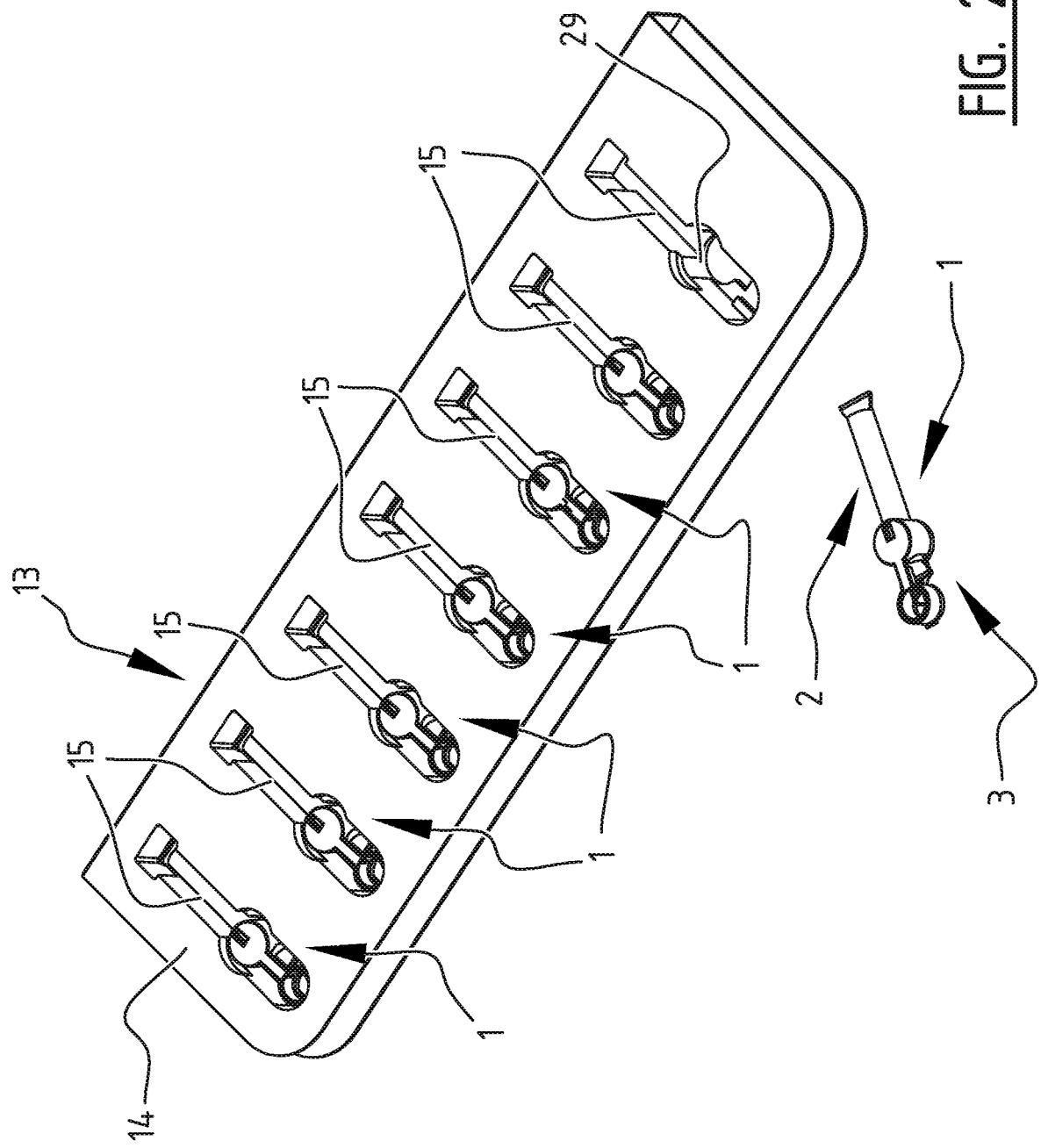

The invention is now elucidated on the basis of a number of embodiments wherein reference is made to the accompanying drawing in which corresponding components are designated with the same reference numerals, and in which:

FIG. 1 is a perspective view of an administering device according to a first embodiment of the invention, FIG. 2 is a front view of the device of FIG. 1, FIG. 3 shows a section along the line III-III in FIG. 2, FIG. 4 is a perspective view of the frame with the perforation member of the administering device of FIG. 1, FIG. 5 is a perspective view of an outer packaging with a number of receiving spaces in which packagings filled with liquid are received, and a frame as shown in FIG. 4, FIG. 6 shows the frame after it has been mounted on one of the packagings in the outer packaging, FIG. 7 shows how the thus formed administering device is taken out of the outer packaging, FIG. 8 is a perspective view of a frame of an administering device according to a second embodiment of the invention, FIG. 9 is a side view of the frame of FIG. 8, FIG. 10 is a top view of the frame of FIGS. 8 and 9, FIG. 11 is a perspective view of the frame of FIGS. 8-10 and a similar packaging as in the first embodiment during a first step of assembly, FIGS. 12 and 13 show a side view and a top view of the packaging and the frame of FIG. 11, FIG. 14 is a perspective view of the administering device, formed by the packaging and the frame of FIGS. 11-13, in a transport position, FIGS. 15 and 16 show a side view and a top view of the administering device of FIG. 14, FIG. 17 is a front view of the administering device of FIG. 14, FIG. 18 shows a section along the line XVIII-XVIII in FIG. 17, FIG. 19 is a perspective view of the administering device of FIGS. 14-18 in the position of use, FIGS. 20, 21 and 22 show a side view, a top view and a front view of the administering device of FIG. 19 in the position of use, FIG. 23 shows a section along the line XXIII-XXIII in FIG. 22, in which the administering device is shown with a drop of liquid, FIG. 24 shows a section along the line XXIV-XXIV in FIG. 20, FIG. 25 is a perspective view of an outer packaging with a number of receiving spaces with administering devices received therein in the transport position according to FIG. 14, and an administering device removed therefrom in the position of use of FIG. 19, FIG. 26 is a partially cross-sectional detail view of an administering device in its transport position in a receiving space of the outer packaging, FIG. 27 is a perspective view of a third embodiment of the administering device according to the invention, FIG. 28 is a perspective view of this administering device from another angle, FIG. 29 is a front view of this embodiment of the administering device, FIG. 30 shows a section along the line XXX-XXX in FIG. 29, and FIG. 31 shows a fourth embodiment of the administering device wherein the packaging takes the form of a bottle with a tubular neck.

A device 1 for administering a liquid, in particular an ophthalmic liquid, drop by drop according to the invention comprises a packaging 2, which is wholly or partially filled with the liquid V, and a frame 3 which can be mounted on packaging 2. Received in frame 3 is an outflow channel 4 which can be connected to packaging 2. Outflow channel 4 comprises at one end a perforation member 5, formed here by the outer end of channel 4 which has been sharpened to a point. This perforation member 5 protrudes through a side wall 6 of packaging 2 when frame 3 is mounted on packaging 2.

In the shown embodiment packaging 2 is formed by a tube or hose which is closed at its ends 7. The tube or hose can be manufactured from a plastic can be closed by welding at the ends 7. Packaging 2 is resiliently deformable to some extent and is clamped between two arms 8 of a U-shaped part of frame 3. The deformability also ensures that side wall 6 forms a liquid-tight closure around perforation member 5. Between the two arms 8 the frame 3 forms a bridge piece 9 through which protrudes outflow channel 4 with perforation member 5. Arms 8 have thickened outer ends 12 which again protrude inward to some extent and by which the tubular packaging 2 is held fixedly so that frame 3 is attached firmly to packaging 2.

The end of channel 4 opposite perforation member 5 is formed as an outflow nozzle 10. The form and dimensions of this outflow nozzle 10 ultimately determine—with given properties of the liquid V—the shape and volume of the drops D which are dispensed. These are very small drops, in the order of 1 to 50 μl, preferably drops with a volume of 2 to 20 μl, and more preferably a volume of 3 to 10 μl. The outer diameter of outflow nozzle 10 amounts here to less than 2 mm, preferably less than 1 mm, and most preferably less even than 0.5 mm The size of outflow nozzle 10 can be designated by a symbol on frame 3 or on an outer packaging to be discussed below. The content of packaging 2 amounts in the shown embodiment to about 150 μl, so that there is sufficient liquid V to dispense one or more test drops before a drop is administered to the eye. The volume is moreover sufficient to administer drops to both eyes of the user.

Contact of the outflow channel 10 with the eye must be avoided. A protective member 11 is therefore arranged in clearance around outflow nozzle 10. In the shown embodiment the protective member 11 is annular and arranged concentrically around outflow nozzle 10. Outflow nozzle 10 is moreover recessed relative to the end edge of the protective member so that it cannot be touched by accident and also cannot come into contact with the eye of the user.

Frame 3 is manufactured from a stiffer material than packaging 2. Frame 3 can for instance be manufactured from a hard plastic such as PP. Outflow channel 4 can be manufactured from steel. An outflow channel of plastic can optionally also be envisaged, which could then be formed integrally with frame 3. A suitable plastic in this case could be PEEK. Plastic frame 3 is formed integrally in this embodiment, for instance by injection moulding or 3-D printing, so including the bridge piece, the arms and the annular protective member. The whole device 1 thus has only three components, packaging 2, the plastic part of frame 3 and the steel outflow channel 4. One or more of these components can otherwise have a colour forming an indication of the nature of the liquid V received therein.

According to an aspect of the invention, administering device 1 is wholly or partially assembled under controlled conditions at a production location and packed there in an outer packaging 13 which can then be supplied to an end user. Outer packaging 3 can be a so-called blister pack with a shell 14 in which recesses 15 are formed which correspond in form and dimensions to packagings 2. In the shown embodiment ten recesses 15 are arranged parallel adjacently of each other in shell 14, although the form and dimensions of shell 14, and thereby the number of recesses 15, can be varied as required. Shell 14 with recesses 15 is covered prior to use with a closing layer—not shown here—for instance a plastic film, aluminium foil or paper. The user must first remove this layer—at least locally—to gain access to one of the packagings 2. Packagings 2 are held in place in outer packaging 13 by this layer, while contamination is prevented. The different components of administering device 1 can be sterilized, for instance by steam or by gamma radiation, prior to being arranged in outer packaging 13 or while they are situated therein.

Recesses 15 have in top view roughly the form of an I. Close to an outer end each recess is provided on either side of packaging 2 with widened parts 16 into which the arms 8 of a frame 3 fit. Frame 3 can thus be clamped round packaging 2 while this packaging 2 lies in recess 15 of outer packaging 13, and is thus held in place. The attachment can hereby be realized very easily without touching packaging 2 or outflow channel 4 with the fingers. Packaging 2 can then be lifted out of recess 15 using the frame 3 attached thereto. The position of frame 3 on packaging 2 is thus determined by the position of the widened portions 16 and will therefore be the same for each administering device 1. As can be seen, frame 3 is arranged close to one of the outer ends 7 of packaging 2 so that a relatively long part of packaging 2 is available to the user for grasping the device 1.

As soon as frame 3 has been mounted on packaging 2, device 1 is ready to use since perforation member 5 has after all then pierced the wall 6 and a liquid connection has been brought about between the interior of packaging 2 and outflow channel 4. Device 1 can only be taken out of outer packaging 13 in this position of use. A drop of the liquid V can then be dispensed by exerting pressure on wall 6 of packaging 2. This drop has precisely determined dimensions and an accurately determined volume which depends on the liquid properties and ambient properties in combination with the dimensions of outflow channel 4 and outflow nozzle 10.

As a consequence of the thickened outer ends 12 of arms 8 the user can feel when frame 3 is properly attached to packaging 2. The risk of leakage due to an incomplete connection is hereby avoided. The dimensioning of arms 8, bridge piece 9 and perforation member 5 is further such that the perforation member does indeed pass through the adjacent wall 6 of packaging 2 but cannot reach the opposite wall 6.

In an alternative, at this moment recommended embodiment of administering device 1 the frame 3 consists of two halves 17 which are connected to each other by means of a hinge 18 (FIG. 8). This frame 3 once again comprises a U-shaped part with two arms 8 and a bridge piece 9 on which perforation member 5 is mounted, and an enclosing part 19 co-acting therewith during use. Enclosing part 19 likewise takes a U-shaped form with two arms 20 and a base 21. Arms 20 of enclosing part 19 are embodied in similar manner to arms 8 of frame 3 according to the first embodiment and thus have a thickened and again inward protruding end part 22. Enclosing part 19 is intended in this embodiment for the purpose of clamping packaging 2, while arms 8 and bridge piece 9 of the U-shaped frame part serve in this embodiment to further enclose packaging 2.

In the shown embodiment arms 20 of enclosing part 19 are provided on the outer side with protrusions 23 which co-act with recesses 24 on the inner side of arms 8 of the U-shaped frame part. Both these components can thus be locked relative to each other when frame 3 is folded round packaging 2, so that packaging 2 can no longer be detached therefrom. This prevents frame 3 being used again.

In this embodiment protective member 11 is embodied in two complementary parts 11A and 11B. One part of the annular protective member is connected by means of a ridge 25 to bridge piece 9 of the U-shaped frame part. Outflow channel 4 extends in this ridge 25 between perforation member 5, which is attached to bridge piece 9, and outflow nozzle 10 which is received in protective ring 11A. The complementary part 11B of the annular protective member 11 is arranged between hinge 18 and enclosing part 19 and is connected thereto via an inclining transition part 26.

Outflow channel 4 is for instance attached by glueing or ultrasonic welding to the plastic components, in particular ridge 25 and bridge piece 9. In this embodiment outflow channel 4 is bent through a right angle at two locations so that perforation member 5 can penetrate at a right angle through wall 6 of packaging 2 and the outflow nozzle 10 coincides with the centre line of the annular protective member 11. Outflow channel 4 thus takes the form of a staple. In order to prevent problems in respect of alignment of nozzle 10 and perforation member 5, these parts of outflow channel 4 are bent only after outflow channel 4 has been attached to ridge 25 and bridge piece 9. The part of outflow channel 4 which must form the outflow nozzle 10 is here easily accessible by a bending tool through the open ring 11. An opening 27 is formed in bridge piece 9 in order to also allow the outer end of channel 4 which must form the perforation member 5 to be reached with a bending tool.

Because ring 11 is open on either side, outflow nozzle 10 is readily visible to both the user and optionally a therapist. The part of the ring facing toward the user can otherwise have a differing colour here, for instance black, so that it is easily discernible to the user. This is particularly important for users who suffer from glaucoma, since they see little contrast.

Protrusions 23 on arms 20 of enclosing part 19 not only make it possible to lock the frame 3 around packaging 2 but also determine a transport position of administering device 1. This transport position is reached by first clamping the packaging 2 in enclosing part 19 (FIG. 11) and then folding the halves 17A, 17B of frame 3 toward each other around hinge 18 until the outer ends of arms 8 rest on protrusions 23 (FIG. 14, 15). In this transport position the perforation member 5 is still remote from wall 6 of packaging 2 so that there is still no liquid connection between outflow channel 4 and packaging 2 (FIG. 18). The position of packaging 2 in frame 3 is otherwise determined in this embodiment by the inclining transition part 26 which forms a stop for the end 7 of packaging 2 (FIG. 12).

In this transport position the administering device 1 can be made available to a user who then need only press bridge piece 9 and enclosing part 19 with some force against each other, whereby arms 8 drop round arms 20 and protrusions 23 snap fixedly into recesses 24. This is an operation which can be performed with one finger, and wherein only the gross motor skills are required. Administering device 1 can therefore also be handled properly by older users. The effecting of the snap connection between bridge piece 9 and enclosing part 19 can moreover be heard and felt by the user so that he/she has confirmation that administering device 1 is ready for use. In this position of use the perforation member protrudes through wall 6 of packaging 2, whereby a liquid connection is once again realized with outflow channel 4. By now again exerting pressure on the part of packaging 2 which protrudes outside frame 3, precisely defined drops can be dispensed as shown schematically in FIG. 23.

As in the case of the first embodiment, this second embodiment of administering device 1 can also be assembled to the transport position at a production location. From here the administering device can then be supplied in an outer packaging 13 to the user. In this embodiment the outer packaging is embodied as a double-folded blister pack having in the shown embodiment seven recesses on either side (FIG. 25), although this number can of course also be varied. The form and dimensions of the recesses once again correspond precisely to those of administering devices 1. In order to prevent the possibility of administering devices 1 being taken out of outer packaging 13 in not yet activated state, means 28 are present in each receiving space 15 for the purpose of fixing arms 8 of frame 3 in outer packaging 13. These fixation means 28 are formed here by protrusions in side walls 29 of each recess 15 which engage in the space between the U-shaped part of frame 3 and enclosing part 19 (FIG. 26). Administering device 1 can only be taken out of outer packaging 13 in activated state when bridge piece 9 is deliberately pressed with force, whereby protrusions 28 of side walls 29 are pressed aside and the U-shaped part or the enclosing part is locked.

Administering device 1 and recess 15 are further formed such that they together define a tilting point 30 (FIG. 20). In the shown embodiment this tilting point 30 is defined by the deepest point of device 1 which rests on the bottom of recess 15, while at least another part of device 1 is clear of this bottom. By pressing on frame 3 on one side of tilting point 30 the packaging 2 is moved upward out of recess 15, whereby it can be easily taken out of the outer packaging.

It is otherwise not essential for outflow nozzle 10 to be oriented parallel to perforation member 5. While this does produce a very simple construction, because all components lie in one plane and are easily accessible, other embodiments can also be envisaged. Outflow channel 4 could thus also be bent halfway along at an angle of for instance 45°, whereby the annular protective member 11 could also be connected at an angle of 45° to bridge piece 9 (FIG. 27). This could for instance result in an ergonomically better position of the part of packaging 2 to be gripped by the user relative to outflow nozzle 10. Enclosing part 19 could in that case be embodied as separate component and need not be connected via a hinge to the rest of frame 3.

It is further not essential for packaging 2 to be wholly tubular. Frame 3 could also be used in combination with a packaging embodied as plastic bottle 31 (FIG. 31), of which only the neck 32 is tubular in the shown embodiment. Such bottles, also referred to as bottle pack, are frequently used in practice.

The invention thus provides an administering device which can be manufactured very easily and at low cost and with which a liquid can be dosed very precisely in discrete drops of very small volume. The embodiment of the administering device according to the invention ensures that the user cannot come into contact in any way whatsoever with the liquid or the components of the construction which come into contact with the liquid, so that the risk of infection is minimized. The administering device is further suitable for assembly under controlled conditions at a production location and for activation by the user with one simple operation.

Although the invention has been elucidated above on the basis of a number of embodiments, it will be apparent that it is not limited thereto but can be varied in many ways. The scope of the invention is therefore defined solely by the following claims.

The invention claimed is:

1. A device for administering a liquid drop by drop, comprising a packaging at least partially filled with the liquid and an outflow channel for connecting to the packaging and comprising a perforation member at one end, wherein the perforation member is received in a frame for mounting on the packaging,
   wherein the packaging is at least partially tubular and the frame can be mounted round the tubular part of the packaging,
   wherein the frame comprises a substantially U-shaped part with two arms which extend on either side of the tubular part of the packaging and a bridge piece connecting the arms and carrying the perforation member,
   wherein the perforation member protrudes through a side wall of the packaging when the frame is mounted on the packaging.

2. The device of claim 1, wherein at least the tubular part of the packaging is resiliently deformable and is clamped between the arms.

3. The device of claim 1, wherein the arms co-act with an enclosing part arranged on a side of the tubular part of the packaging opposite the bridge piece.

4. The device of claim 3, wherein the arms are movable relative to the enclosing part between a transport position, in which the outflow channel is not yet connected to the packaging, and a position of use in which the perforation member of the outflow channel protrudes into the packaging.

5. The device of claim 4, wherein the arms are locked relative to the enclosing part in the position of use.

6. The device of claim 1, wherein the outflow channel has at an end opposite the perforation member an outflow nozzle which is received with clearance and recessed into a protective member which forms part of the frame.

7. The device of claim 6, wherein the protective member takes the form of a ring.

8. The device of claim 7, wherein a center line of the ring is parallel to or coincides with the outflow nozzle.

9. The device of claim 6, wherein the outflow channel is substantially straight and the protective number lies substantially in line with a part of the frame mounted on the packaging.

10. The device of claim 6, wherein the outflow channel has at least one bend and the protective member is open.

11. The device of claim 10, wherein the frame has an opening through which the perforation member is accessible.

12. The device of claim 10, wherein the protective member is connected to a part of the frame carrying the perforation member, and the outflow channel extends between this frame part and the protective member.

13. The device of claim 6, wherein the protective member, the bridge piece and the arms are formed as one body, and the outflow channel is attached to this body or integrated therein.

14. The device of claim 13, wherein an enclosing part is connected pivotally to the body.

15. The device of claim 14, wherein the enclosing part is formed integrally with the body.

16. The device of claim 6, further comprising a first half comprising an enclosing part and a part of the protective member, and a second half which is connected pivotally thereto and comprises a complementary part of the protective member and the bridge piece and the arms.

17. The device of claim 1, wherein the frame is manufactured from a stiffer material than the packaging.

18. An assembly of the administering device of claim 1 and an outer packaging which comprises a receiving space for the administering device.

19. The assembly of claim 18, wherein the receiving space comprises a recess for the packaging and a recess for at least a part of the frame which are formed in a surface.

20. The assembly of claim 18, wherein the receiving space is configured to fix the administering device therein as long as it is in a transport position and not ready for use.

21. The assembly of claim 20, wherein the fixation means comprise a deformable part of the wall of the receiving space.

22. The assembly of claim 18, wherein the frame and a part of the receiving space define a tilting point.

23. The assembly of claim 18, wherein the outer packaging comprises a plurality of receiving spaces as well as space for arranging an information carrier or printed information.

24. A method for administering a liquid drop by drop, by taking the administering device of claim 1 in the hand, mounting the frame on the packaging, wherein the perforation member pierces a wall of the packaging and brings about a connection between the interior of the packaging and the outflow channel, positioning the device above a recipient and exerting pressure on the packaging in order to urge the liquid dropwise therefrom.

25. The method of claim 24, wherein the pressure is exerted on a deformable part of the wall of the packaging.

26. The method of claim 24, wherein the frame is connected to the packaging in a transport position in which the outflow channel has not yet been connected to the interior of the packaging, and is mounted on the packaging by being displaced to a position of use in which the perforation member protrudes into the packaging.

27. The method of claim 24, wherein the administering device is received in a receiving space in an outer packaging and the frame is mounted on the packaging while the packaging is situated in the receiving space.

28. The method of claim 24, wherein the channel comprises an outflow nozzle surrounded by an open protective member and administering is monitored by being observed from a side of the protective member lying opposite the outflow nozzle.

29. The device of claim 1, wherein the liquid is an ophthalmic liquid.

30. The method of claim 24, wherein the liquid is an ophthalmic liquid.

\* \* \* \* \*